(12) United States Patent
Deimling

(10) Patent No.: US 6,888,350 B2
(45) Date of Patent: May 3, 2005

(54) MEDICAL APPARATUS AND COMPUTER PROGRAM PRODUCT FOR MAGNETIC RESONANCE IMAGING WITH INTERACTIVE CONTRAST OPTIMIZATION

(75) Inventor: Michael Deimling, Moehrendorf (DE)

(73) Assignee: Siemens Aktiengesellschaft, Munich (DE)

( * ) Notice: Subject to any disclaimer, the term of this patent is extended or adjusted under 35 U.S.C. 154(b) by 186 days.

(21) Appl. No.: 10/292,659

(22) Filed: Nov. 13, 2002

(65) Prior Publication Data

US 2003/0092981 A1 May 15, 2003

(30) Foreign Application Priority Data

Nov. 14, 2001 (DE) .......................................... 101 55 790

(51) Int. Cl.[7] ................................................. G01V 3/00
(52) U.S. Cl. ...................................... 324/309; 324/307
(58) Field of Search ............................... 324/309, 307, 324/308, 312, 318; 600/413; 378/19, 62

(56) References Cited

U.S. PATENT DOCUMENTS

| | | | | |
|---|---|---|---|---|
| 5,786,693 A | * | 7/1998 | Gullapalli et al. | .......... 324/309 |
| 6,121,775 A | * | 9/2000 | Pearlman | ..................... 324/309 |
| 6,192,264 B1 | * | 2/2001 | Foo et al. | ................... 600/413 |
| 6,456,071 B1 | | 9/2002 | Hennig | |
| 6,470,071 B1 | * | 10/2002 | Baertsch et al. | .............. 378/62 |
| 6,504,895 B1 | * | 1/2003 | Dixon et al. | .................. 378/19 |
| 6,552,542 B1 | * | 4/2003 | Overall | ....................... 324/309 |
| 6,636,038 B1 | | 10/2003 | Heid | |

* cited by examiner

Primary Examiner—Brij B. Shrivastav
(74) Attorney, Agent, or Firm—Schiff Hardin LLP

(57) ABSTRACT

In a magnetic resonance tomography apparatus and method, whereby an interactive contrast optimization is implemented by defining a multi-contrast sequence for exciting nuclear spins in a slice of a subject to be measured, defining parameters characteristic of the sequence, measuring a number of contrast versions of the slice in the form of raw data with the previously defined sequence, processing the raw data of the slice, and thereby generating a number of images of the slice that differ in contrast from one another and generating an image with improved contrast on the basis of an interactive real-time contrast variation of the images acquired by the multi-contrast sequence, via a user interface.

12 Claims, 3 Drawing Sheets

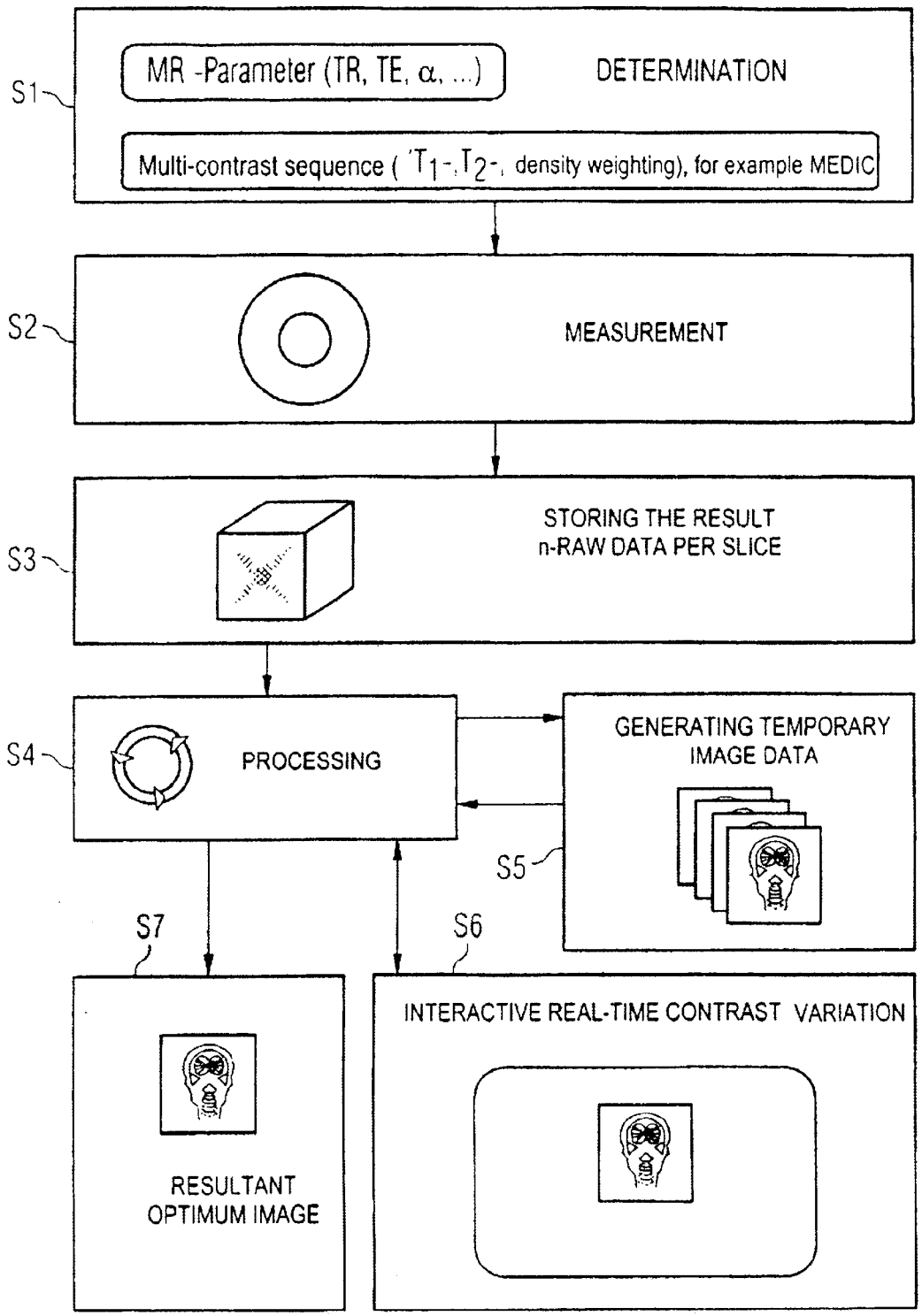

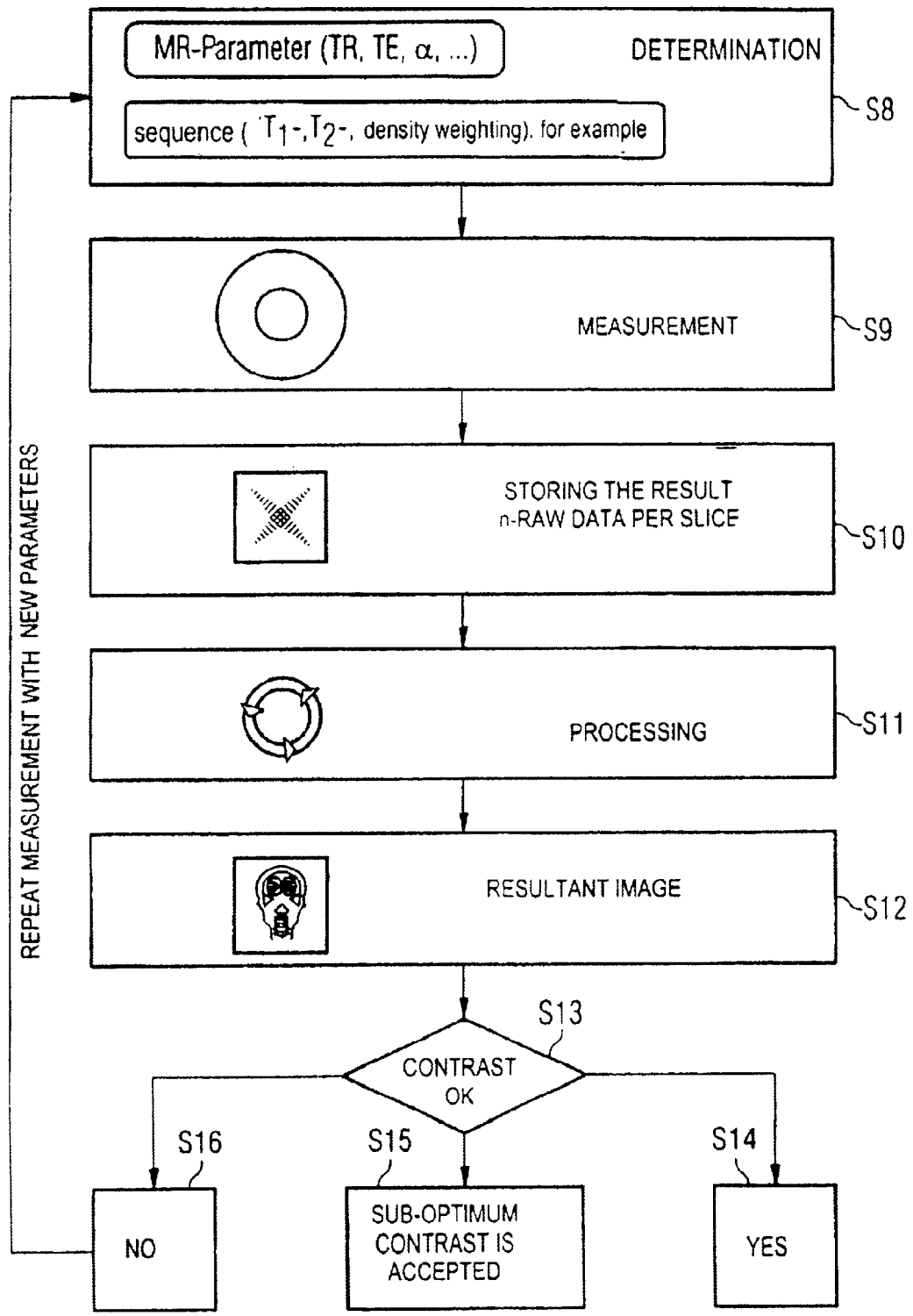

MEDICAL APPARATUS AND COMPUTER PROGRAM PRODUCT FOR MAGNETIC RESONANCE IMAGING WITH INTERACTIVE CONTRAST OPTIMIZATION

BACKGROUND OF THE INVENTION

1. Field of the Invention

The present invention is directed in general to magnetic resonance tomography as employed in medicine for examining patients. The present invention is specifically directed to a method for magnetic resonance imaging as well as to a magnetic resonance tomography apparatus for the implementation of this method, wherein an interactive contrast optimization is implemented.

2. Description of the Prior Art

MRT is based on the physical phenomenon of nuclear magnetic resonance and has been successfully utilized as an imaging method in medicine and biophysics for more than 15 years. In this examination method, the subject is exposed to a strong, constant magnetic field. As a result, the nuclear spins of the atoms in the subject align, the spins having been previously irregularly oriented. Radio-frequency energy can then excite these "ordered" nuclear spins to a specific oscillation. This oscillation generates the actual measured signal in MRT, which is picked up with suitable reception coils. The measurement subject can be spatially encoded in all three spatial directions by utilizing non-homogeneous magnetic fields generated by gradient coils. A free selection of the slice to be imaged is possible, so that tomograms of the human body can be registered in all directions. In medical diagnostics, MRT is particularly distinguished as a tomographic imaging method as being a "non-invasive" examination with a versatile contrast capability. Due to the excellent presentation of soft tissue, MRT has developed into a method that is often superior to X-ray computer tomography (CT).

One of the principal advantages of MR tomography is the excellent ability to display of soft tissue, i.e. an excellent soft part contrast in the reconstructed MRT images. The reason for this is the different relaxation times T1 (of the longitudinal magnetization) and T2 (of the transverse magnetization) as well as T2* (effective relaxation time of the transverse magnetization) of the tissue that reflect the interaction of the hydrogen nuclei with their environment in a complex way. However, the proton densities p also play a certain part in the MRT imaging. The term "proton density" means that part of the tissue protons whose magnetic resonance signal contributes to the MR image signal. These are essentially the water protons and the methyl protons of the mobile fatty acids. Hydrogen nuclei in cell membranes, proteins or in other relatively rigid macromolecules generally do not contribute to the MRT signal; their signal usually already has decayed to zero at the point in time of the data acquisition.

Whereas the image contrast of a CT image is dependent only on the electron density of the observed tissue, the magnetic resonance signal, and thus the character of the MRT image, is determined by the three tissue-specific parameters $\rho$, T1, T2 and T2* as well as by the type of pulse sequence employed and the corresponding exposure parameters. This variability of the MRT signal offers the possibility of optimizing the image contrast between specific tissue structures with a suitable selection of the pulse sequence and the exposure parameters. In this way, there is the possibility of achieving an optimally good differentiation between specific tissue structures—for example, healthy tissue and tumor tissue.

According to the prior art, for example in clinical practice, MRT images are being acquired with different exposure parameters that are selected such that the image contrast of the individual images is mainly determined by a single tissue parameter. Images of this type are made in this context of T1, T2, T2* or $\rho$ weighted images.

FIG. 3 shows such a method according to the prior art. In step S8, a specific imaging sequence is selected (for example, T1, T2, or $\rho$ weighted) and the determination of the parameters characterizing the sequence (for example, repetition time TR, echo time TE, flip angle a, etc. are determined). The measurement subsequently ensues in step S9, the raw data of the measured slice according to step S10 being generated therewith. The raw data, which are present in the form of a matrix, are processed in a computer in step S11 (including Fourier transformation) and are presented to the user as MRT image according to step S12—usually at a picture screen. In step S13, the user must then make a decision as to whether the contrast of the image satisfies the requirements for the diagnosis (step S14). A sub-optimum contrast of the image can be accepted according to step S19. If the contrast of the image is inadequate, the measurement according to step S16 is repeated with other parameters, possibly with a different sequence type as well (begin again with step S8), until an image having adequate quality in terms of the contrast has been generated.

A disadvantage of this known method is that it is dependent on the resulting contrast weighting of the selected sequence and no targeted contrast improvement is possible. Additionally, this type of contrast optimization is decidedly time-consuming since all of the above-recited steps must be repeated as warranted.

SUMMARY OF THE INVENTION

An object of the present invention is to provide a method and an apparatus for magnetic resonance imaging allowing improved contrast formation.

This object is inventively achieved in a method for the optimization of MRT images including the steps of defining a multi-contrast sequence for exciting nuclear spins in a slice of a subject to be measured, defining parameters characteristic of the sequence, measuring the raw data of the slice and thereby generating a number of images of the slice that differ in contrast from one another; and generating an image with optimum contrast on the basis of an interactive real-time contrast variation by selective combinations of the images acquired by the multi-contrast sequence in real time, via a user interface.

The interactive real-time contrast variation inventively ensues by pixel operations with operation algorithms.

It is thereby advantageous for the interactive real-time contrast variation to ensue at a monitor.

In another embodiment, the interactive real-time contrast variation ensues via a switch, the switch being designed as a software tool on the monitor.

It also can be advantageous to implement further measurements of the slice with different sequences or different sequence parameters in parallel with the interactive real-time contrast variation, so that further, temporary images of the slice are made available. This embodiment of the method yields a great timesaving in the generation of an optimum image contrast.

The above object also is achieved in accordance with the invention in a magnetic resonance tomography apparatus for the implementation of the above-described method.

The above object also is achieved in accordance with the invention in a computer software product that implements an above-described method when it runs on a computer device connected to a magnetic resonance tomography apparatus.

DESCRIPTION OF THE DRAWINGS

FIG. 2 schematically shows the inventive method.

FIG. 3 schematically shows a method according to the prior art.

DESCRIPTION OF THE PREFERRED EMBODIMENTS

Figure 1:
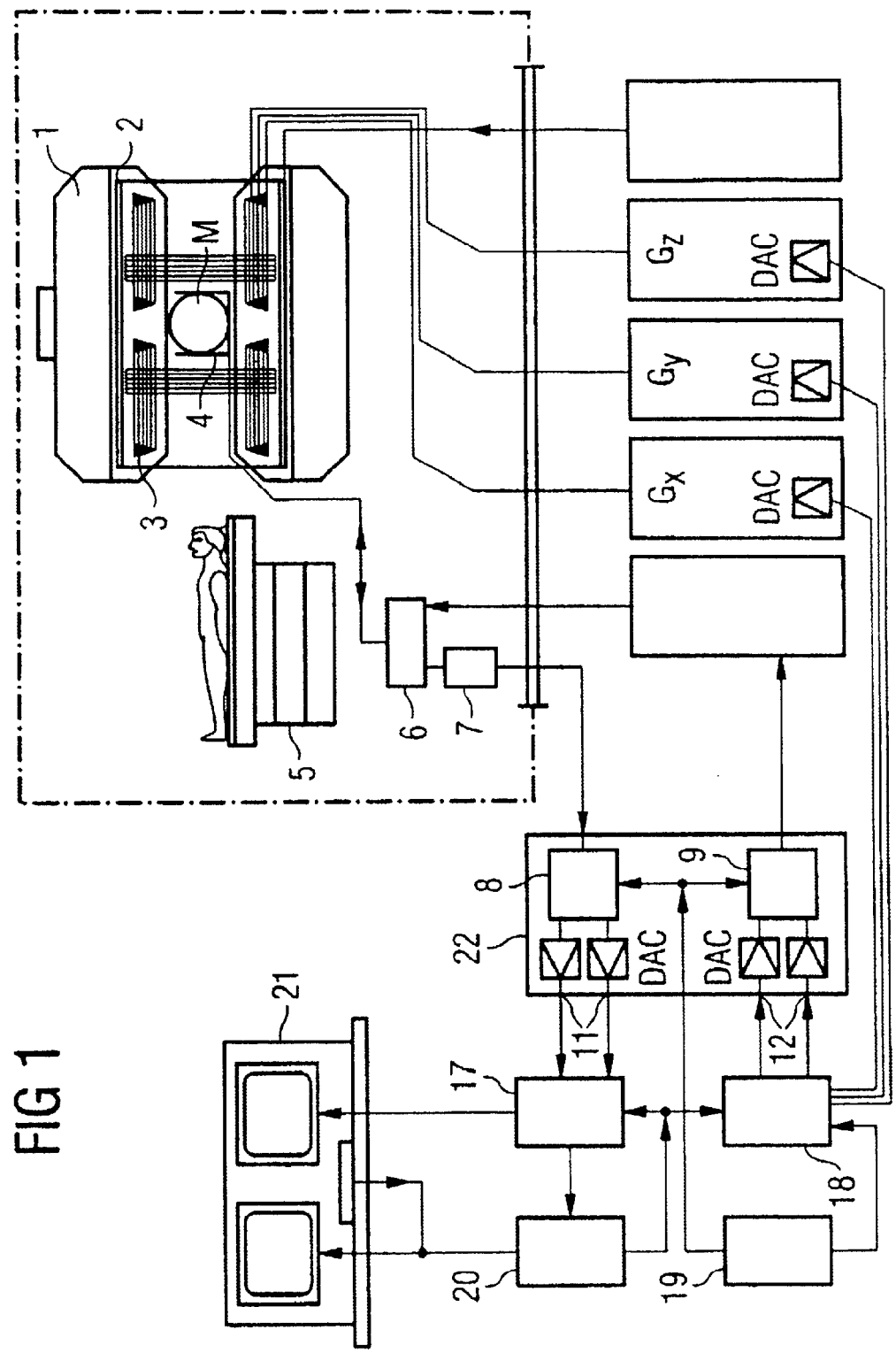
FIG. 1 is a schematic illustration of an inventive magnetic resonance imaging (magnetic resonance tomography) apparatus.

FIG. 1 is a schematic illustration of a magnetic resonance imaging (magnetic resonance tomography) apparatus for generating a magnetic resonance image of a subject according to the present invention. The basic components of the magnetic resonance tomography apparatus corresponds to those of a conventional tomography apparatus, with the differences described below. A basic field magnet 1 generates a temporally constant, strong magnetic field for the polarization or alignment of the nuclear spins in the examination region of a subject such as, for example, part of a human body to be examined. The high homogeneity of the basic magnetic field required for the magnetic resonance measurement is defined in a spherical measurement volume M into which the parts of the human body to be examined are introduced. For supporting the homogeneity demands and, in particular, for eliminating time-invariable influences, shim plates of ferromagnetic material are attached at suitable location. Time-variable influences are eliminated by shim coils 2 that are driven by a shim power supply 15.

A cylindrical gradient coil system 3 that is composed of three coils is introduced into the basic field magnet 1. Each coil is supplied with power by an amplifier 14 for generating a linear gradient field in the respective direction of the Cartesian coordinate system. The first coil of the gradient field system 3 generates a gradient $G_x$ in the x-direction, the second coil generates a gradient $G_y$ in the y-direction and the third coil generates a gradient $G_z$ in the z-direction. Each amplifier 14 includes a digital-to-analog converter that is driven by a sequence controller 18 for generating gradient pulses at the correct time.

Disposed within the gradient field system 3 is a radio-frequency antenna 4 that converts the radio-frequency pulses supplied by a radio-frequency power amplifier into a magnetic alternating field for exciting the nuclei and aligning the nuclear spins of the examination subject, or of the region under examination in the subject. The radio-frequency antenna 4 is composed or one or more RF transmission coils and one or more RF reception coils, possibly composed of an arrangement of component coils (generally called "coil arrays" or "phased array coils"). The RF reception coils of the radio-frequency antenna 4 also convert the alternating field emanating from the precessing nuclear spins, i.e. the nuclear magnetic resonance echo signals usually produced by a pulse sequence composed of one or more radio-frequency pulse and one or more gradient pulses, into a voltage that is supplied via an amplifier 7 to a radio-frequency reception channel 8 of a radio-frequency system 22. The radio-frequency system 22 further has a transmission channel 9 in which the radio-frequency pulses for the excitation of the nuclear magnetic resonance are generated. The respective radio-frequency pulses are thereby presented digitally as a sequence of complex numbers on the basis of a pulse sequence in the sequence controller 18 prescribed by the system computer 20. As real part and an imaginary part, this number sequence is supplied via respective inputs 12 to a digital-to-analog converter in the radio-frequency system 22 and is supplied therefrom to a transmission channel 9. In the transmission channel 9, the pulse sequences are modulated on a radio-frequency carrier signal having a base frequency corresponds to the resonant frequency of the nuclear spins in the measurement volume.

The switching from transmission mode to reception mode ensues via a transmission-reception diplexer 6. The RF transmission coil of the radio-frequency antenna 4 emits the radio-frequency pulses for the excitation of the nuclear spins into the measurement volume M and samples resultant echo signals via the RF reception coils. The correspondingly acquired magnetic resonance signals are phase-sensitively demodulated in the reception channel 8 of the radio-frequency system 22 and are converted via respective analog-to-digital converters into a real part and an imaginary part of the measured signal. An image computer 17 reconstructs an image from the measured data acquired in this way. The administration of the measured data, the image data and the control programs ensues via a system computer 20. On the basis of a prescription with control programs, the sequence controller 18 controls the generation of the respectively desired pulse sequences and the corresponding sampling of k-space. In particular, the sequence controller 18 controls the temporally correct switching of the gradients, the emission of the radio-frequency pulses with defined phase and amplitude, as well as the reception of the magnetic resonance signals. The time basis for the radio-frequency system 22 and the sequence controller 18 is made available by a synthesizer 19. The selection of corresponding control programs for generating a nuclear magnetic resonance image as well as the display of the generated nuclear magnetic resonance image ensues via a console 21 that has a keyboard as well as one or more picture screens.

Inventively, the apparatus operates in the following way, with reference to FIG. 2.

As described above, a previously defined multi-contrast sequence is generated according to step S1 in the transmission channel 9 via the system computer 20 and the sequence controller. A number of images of the slice of a subject to be examined that differ in view of their contrasts and generated by means of this sequence. Examples of possible multi-contrast sequences are set forth below (in the form of acronyms for MR sequences that are employed for specific inquiries with adapted parameters), with the weighting types are also indicated for most:

TSE (turbo spin echo with multiple contrast (shared echo): $\rho, T_2$,

DESS (double echo steady state): $T_2$

HASTE (half Fourier RARE double contrast): $T_2$,

MEDIC (multi echo data image combination): $T_2^*$,

HIRE (high intensity reduction, "dark fluid"): $T_2$,

SINOP (simultaneous Inphase out of phase): $T_1$,

Interleaved fat water dual spin echo

This last method was first published by Kwok et al. in The Journal of Magnetic resonance 13:318–323 2001).

In addition to the definition of the sequence type, the definition of the parameters characterizing this sequence type also ensues in step S1, for instance repetition time TR, echo time TE, flip angle α, etc. For example, one of the above-recited multi-contrast sequences is selected as the sequence type. A multi-contrast sequence is characterized by at least two or more echoes, and thus at least two or, respectively, more successive images of the same slice being generated, following the magnetic resonance excitation in the subject, by means of one or more suitable radio-frequency pulses, or by means of suitable gradient switching. Care is thereby exercised to make sure that multi-contrast sequences are employed wherein the images of the successive echoes generally differ from one another by means of highly different contrasts. In, for example, a $T_2$ weighted image, fluids such as, for example, ventricle (i.e. fluid-filled cavities in the brain) have very pronounced contrast in addition to musculature and fat tissue. An echo following 100 to 300 ms after the first spin excitation, however, generates an image wherein only fluid structures are still visible due to the short, exponentially decaying T2 relaxation of the spins of fat tissue and muscle tissue.

The goal is to make good use of this pronounced contrast difference of the measured images. For example, by subtracting the pure fluid image from the image measured first—such an image subtraction will be explained below,—an image is obtained wherein the contrast of muscle, cartilage and fat tissue appears much more clearly.

When, thus, a number of contrast versions of a slice have been measured in step S2 as a result of the selected multi-contrast sequence, raw data matrices of the measured slice corresponding to the different versions are generated in step S3. In step 4, these raw data matrices are processed in the system computer (including Fourier transformation) and are stored in step S5 in the memory of the image computer 17 or of the system computer 20 in the form of MRT images, for example as temporary images. One or more of these images can then be presented to the user as MRT image, usually at a picture screen.

In step S6, the user now has the possibility of operating the measured MRT images presented on the picture screen, and differing in contrast, according to the user's own considerations. This ensues, for example, by a selection of the images as well as a selection of the desired mode of operation via a mouse click at one or more switches (sliders) at the monitor, fashioned as software tools. The function "Center/Window" is known (center indicates the height of the image presentation and window the width). If, for example, the user would like to subtract Image B from image A with corresponding weighting (for example, 0.5), the user clicks on image A, then clicks on an icon (symbol on the picture screen) representing to the subtraction algorithm and, finally, clicks on the image B. The image processing operation A—0.5*B is then implemented by means of pixel operations in the background, i.e. in the image computer 17 or system computer 29. Operation algorithms such as addition, subtraction, multiplication, logarithmization, self-weighting (with which the signal-to-noise ratio can be improved), square sum averaging (sum of square, SOS), high-pass filter, low-pass filter, etc., are conceivable.

The processed, resultant image with optimum contrast is then saved in an archive in step S7.

In another embodiment of the present invention, further measurements of the slice with other sequence types or, respectively, other sequence parameters can be implemented in parallel with the user's interactive real-time contrast variation at the monitor, and thus further temporary images of the slice can be made available. An even greater number of different images thus can be generated and the number of contrast combinations can be increased by a multiple.

The image post-optimization (post-processing) with the inventive method and the inventive magnetic resonance tomography apparatus ensues about as fast as a multi-planar reconstruction (MPR).

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for operating a magnetic resonance tomography apparatus comprising the steps of:
    defining a multi-contrast sequence for exciting nuclear spins in a slice of a subject;
    defining parameters characteristic of said sequence;
    obtaining raw data from said slice by executing said sequence, and from said raw data, generating a plurality of images of said slice having respectively different contrast; and
    selectively combining said images with respectively different contrast in an interactive, real-time contrast variation via a user interface to generate an image with an optimum contrast.

2. A method as claimed in claim 1 wherein said images with respectively different contrast are each composed of pixels, and comprising conducting said interactive real-time contrast variation by operations on said pixels with at least one operation algorithm.

3. A method as claimed in claim 1 comprising conducting said interactive, real-time contrast variation by displaying said images with respectively different contrast at a picture screen of said user interface.

4. A method as claimed in claim 1 comprising conducting said interactive real-time contrast variation by actuating a switch at said user interface.

5. A method as claimed in claim 1 comprising the additional step of obtaining further raw data from said slice with at least one further sequence conducted in parallel with said interactive, real-time contrast variation and thereby making temporary images of said slice available at said user interface for inclusion in said interactive real-time contrast variation.

6. A method as claimed in claim 1 comprising the additional step of obtaining further raw data from said slice with further parameters conducted in parallel with said interactive, real-time contrast variation and thereby making temporary images of said slice available at said user interface for inclusion in said interactive real-time contrast variation.

7. A magnetic resonance tomography apparatus comprising:
    a system computer wherein a multi-contrast sequence for exciting nuclear spins in a slice of a subject is defined, and wherein parameters characteristic of said sequence are defined;
    a magnetic resonance scanner operated by said system computer to execute said multi-contrast sequence to obtain raw data of said slice;
    said system computer processing said raw data to generate a plurality of images of said slice with respectively different contrast; and
    a user interface connected to said system computer at which said plurality of images are displayed, and having a user actuatable input allowing said plurality of images to be selectively combined in real-time interactive contrast variation to generate a contrast-optimized image from said plurality of images.

8. A magnetic resonance tomography apparatus as claimed in claim 7 wherein each image in said plurality of images is composed of pixels, and wherein said system computer implements said interactive, real-time contrast variation by operations on said pixels with at least one operation algorithm.

9. A magnetic resonance tomography apparatus as claimed in claim 8 wherein said plurality of images are displayed at a picture screen of said user interface.

10. A magnetic resonance tomography apparatus as claimed in claim 7 wherein said user interface has a user actuated switch, and wherein said plurality of images are combined by actuation of said switch.

11. A magnetic resonance tomography apparatus as claimed in claim 7 wherein said system computer defines further sequences for exciting nuclear spins in said slice and controls said magnetic resonance scanner to execute said further sequences in parallel with said multi-contrast sequence to obtain further raw data, and wherein said system computer processes said raw data obtained from said multi-contrast sequence and said raw data obtained from said further sequence in parallel in said real-time interactive contrast variation to generate said contrast-optimized image.

12. A computer program product loadable into a computer of a magnetic resonance tomography apparatus for operating said computer for defining a multi-contrast sequence for exciting nuclear spins in a slice of a subject, defining parameters characteristic of said sequence, obtaining raw data from said slice by executing said sequence, and from said raw data, generating a plurality of images of said slice having respectively different contrast; and selectively combining said images with respectively different contrast in an interactive, real-time contrast variation via a user interface to generate an image with an optimum contrast.

* * * * *